US006428180B1

(12) United States Patent
Karram et al.

(10) Patent No.: US 6,428,180 B1
(45) Date of Patent: Aug. 6, 2002

(54) SURGICAL ILLUMINATION DEVICE AND METHOD OF USE

(76) Inventors: Mickey M. Karram, 8700 Old Indian Hill Rd., Cincinnati, OH (US) 45243; Bryan D. Knodel, P.O. Box 22024, Flagstaff, AZ (US) 86002

( * ) Notice: Subject to any disclaimer, the term of this patent is extended or adjusted under 35 U.S.C. 154(b) by 0 days.

(21) Appl. No.: 09/620,368

(22) Filed: Jul. 20, 2000

Related U.S. Application Data (60) Provisional application No. 60/144,857, filed on Jul. 20, 1999, and provisional application No. 60/206,792, filed on May 24, 2000.

(51) Int. Cl.[7] ................................................. F21S 2/00
(52) U.S. Cl. ........................ 362/119; 362/109; 362/120
(58) Field of Search ............................... 362/109, 115, 362/118, 120, 119, 187, 188; 606/2, 13–17; 607/88, 92

(56) References Cited

U.S. PATENT DOCUMENTS

| | | | | |
|---|---|---|---|---|
| 611,038 A | | 9/1898 | Lohman ..................... 27/24.1 |
| 1,082,887 A | * | 12/1913 | Maisel ........................ 362/187 |
| RE15,022 E | * | 1/1921 | Burgess ...................... 362/187 |
| 2,029,487 A | | 2/1936 | Kleine |
| 2,515,292 A | * | 7/1950 | Carr ........................... 294/65.5 |
| 2,854,564 A | * | 9/1958 | Cohen et al. ............... 362/119 |
| 3,019,790 A | | 2/1962 | Militana ..................... 606/108 |
| 3,023,306 A | | 2/1962 | Kester ........................... 240/2 |
| 3,881,468 A | | 5/1975 | Foltz .......................... 128/23 |
| 3,919,541 A | * | 11/1975 | Chao ........................... 362/120 |
| 3,980,086 A | | 9/1976 | Kletschka et al. .......... 128/318 |
| 4,244,947 A | | 1/1981 | Abraham et al. ............ 424/177 |
| 4,329,737 A | | 5/1982 | Triller et al. ................. 362/32 |
| 4,542,741 A | * | 9/1985 | Burgin ........................ 606/167 |
| 4,562,832 A | | 1/1986 | Wilder et al. ................ 128/20 |
| 4,577,263 A | * | 3/1986 | Maglica ...................... 362/187 |
| 4,605,990 A | | 8/1986 | Wilder et al. ................. 362/32 |
| 4,759,348 A | | 7/1988 | Cawood ......................... 128/6 |
| 5,004,469 A | | 4/1991 | Palmieri et al. ............. 606/139 |
| 5,037,433 A | | 8/1991 | Wilk et al. .................. 606/139 |
| 5,086,378 A | | 2/1992 | Prince ......................... 362/103 |
| 5,147,356 A | | 9/1992 | Bhatta .......................... 606/37 |
| 5,217,460 A | | 6/1993 | Knoepfler ..................... 606/52 |
| 5,353,786 A | | 10/1994 | Wilk ............................ 128/23 |
| 5,448,459 A | * | 9/1995 | Rogers ........................ 362/191 |
| 5,571,071 A | | 11/1996 | Shapiro ....................... 600/187 |
| 5,632,740 A | | 5/1997 | Koch et al. ..................... 606/4 |
| 5,683,436 A | | 11/1997 | Mendes et al. ............... 607/88 |
| 5,785,408 A | * | 7/1998 | Tseng ......................... 362/119 |
| 5,820,249 A | | 10/1998 | Walsten et al. ............. 362/191 |
| 5,921,654 A | * | 7/1999 | Coyle .......................... 362/120 |
| 5,951,142 A | * | 9/1999 | Wang et al. ................. 362/109 |
| 5,964,732 A | | 10/1999 | Willard ....................... 604/117 |
| 6,028,694 A | | 2/2000 | Schmidt ...................... 359/264 |
| 6,048,073 A | | 4/2000 | Shaio ........................... 362/120 |
| 6,116,747 A | * | 9/2000 | Grawameyer et al. ...... 362/119 |

* cited by examiner

*Primary Examiner*—Sandra O'Shea
*Assistant Examiner*—Ismael Negron
(74) *Attorney, Agent, or Firm*—Chittaranjan N. Nirmel (57) ABSTRACT

A compact, self-powered, selectively-mountable lighting unit provides light directable by a user to an operation site in a confined space to enable the user to operate a tool therein. The lighting unit is detachably mountable in a variety of ways either to a user-selected location on any suitable surgical instrument, or at the user's option to an adjacent location within the confined space, to facilitate well-lit and accurate viewing thereat. The lighting unit may be adapted to provide lighting of selected frequency, in an adjustable focus ranging from substantially diffuse light to a tightly focused beam. A known dead-soft element may be included to enable the user to adjust orientation of the delivered light.

27 Claims, 6 Drawing Sheets

SURGICAL ILLUMINATION DEVICE AND METHOD OF USE

This application claims priority to U.S. Provisional Patent Application Ser. No. 60/144,857 of Dr. Mickey M. KARRAM et al. titled "NEEDLE-HOLDER WITH INTEGRAL SELF-CONTAINED LIGHTING AND IRRIGATION MECHANISM" filed Jul. 20, 1999, and to U.S. Provisional Patent Application Ser. No. 60/206,792 of Dr. Mickey M. KARRAM et al. titled "SURGICAL ILLUMINATION DEVICE AND METHOD OF USE" filed May 24, 2000.

FIELD OF THE INVENTION

This invention relates to a compact, self-powered, selectively mountable lighting unit to provide lighting within a confined space to enable a user to operate a tool therein. More particularly, the invention relates to such a lighting unit formed to be mounted at a user's option to a surgical instrument applied by the user to an operation site within a confined space inside a patient's body so as to light a region at and about the operation site or, in the alternative, to be mounted to the patient's tissue adjacent the operation site to light the same.

BACKGROUND OF THE RELATED ART

Adequate lighting of an operation site is of great importance for any surgical procedure. Currently, many such procedures, including, but not limited to, incision, suturing, clamping, cauterizing, irrigating, and various forms of tissue manipulation within a patient's body, are often performed under overhead lighting of high intensity. In particular circumstances, this is not adequate, and surgeons sometimes utilize a light mounted to a harness worn on the head and intended to direct light forwards to facilitate viewing of the operation site where the surgeon is applying surgical instruments.

In certain kinds of surgery, e.g., urogynecological surgery, the surgeon has to operate deep within the patient's pelvis, and neither overhead lighting nor a head-mounted light is satisfactory. The surgery typically involves operations performed through the patient's vagina, and the provision of adequate light to the operation site is very difficult at all times, and particularly so if the patient is obese. In such surgery, the surgeon cannot even benefit from the assistance of a skilled helper, simply because all significant activity occurs within a confined space, where quick action based on clear viewing is very important to address eventualities, such as bleeding and related blood clot formations. Various devices have been suggested to date, but none are considered satisfactory. Known solutions to the general problem of lighting surgical sites include the following.

U.S. Pat. No. 2,029,487 to Kleine, titled "Illuminated Cautery Electrode," teaches an illuminating device clamped to each of two-current bearing electrodes of a cautery instrument to be powered thereby. This invention was patented in 1934, and cautery instruments have changed significantly since then, besides which many surgical instruments are not electrically powered in any way.

U.S. Pat. No. 5,553,786 to Wilk, titled "Surgical Lighting Method," teaches a remotely located light source coupled by an optical fiber to a flexible lighting unit mountable to a retractor or adhered to the skin of a patient. The presence of an electrical cable or optical fiber within the confines of a patient's vagina is awkward and therefore undesirable during most urogynaecological surgical operations.

U.S. Pat. No. 4,605,990 to Wilder et al., titled "Surgical Clip-on Light Pipe Illumination Assembly," teaches a remote light source from which light is conveyed via a flexible pipe clamped to a patient's tissue and out of a "dead soft" end bendable by the user to direct emitted light as desired. The presence of a light pipe of this kind is not acceptable in very confined spaces, for reasons discussed earlier.

U.S. Pat. No. 3,881,468 to Foltz, titled "Flex Light," teaches a self-powered light-producing device from which light is emitted at the distal end of an elongate portion. The device may be of use in certain kinds of surgery, but is clearly intended to be held in a user's hand, and is therefore not suitable for convenient lighting in confined spaces, where any impediments to a surgeon's viewing and simultaneous freedom to operate are critical.

U.S. Pat. No. 6,028,694 to Schmidt, titled "Illumination Device Using Pulse Width Modulation of a LED," addresses a related problem, namely, the provision of electromagnetic energy in the visible spectrum for lighting delicate tissues during lengthy surgical procedures. The suggested pulse-powering of the light emitting diode (LED) obviously has merits that may be acceptable if the associated costs and ease of operation are reasonable.

The problem addressed by the present invention is serious and is one of long standing, and the solution offered herein overcomes the shortcomings of the prior art affordably.

SUMMARY OF THE INVENTION

It is a principal object of this invention to provide a compact, self-powered, selectively mountable lighting unit to provide lighting within a confined space to enable a user to operate a tool therein.

Another object is to provide a surgeon with adequate lighting of an operation site within a confined space in a patient's body with a compact, self-powered, selectively-mountable lighting unit that will provide light of selected focus for at least a predetermined duration.

A related object of this invention is to provide a tool having an operating distal end that is to be used within a confined space, where a user will require lighting at and about the distal end with a self-powered, compact lighting unit mounted to the tool itself within the confined space.

Another related object is to provide a method of providing lighting at an operation site within a confined space, to enable a user to operate the tool therein.

These and other related objects of this invention are realized by providing a compact, self-powered, lighting unit detachably mountable to any surgical tool at a location selected thereon by a user, to provide lighting within a confined space containing a surgical site to enable the user to operate the surgical tool thereat, comprising:
  a housing containing a power source;
  a switchable circuit;
  a light-generating element powered by the power source via the circuit; and
  a mounting mechanism attached to the housing, to enable the lighting unit to be mounted to the surgical tool at the selected location thereon to provide lighting at and about the surgical site.

In another aspect of the invention there is provided an improved surgical tool having an operating distal end that is to be used within a confined space where a user will require lighting at and about the distal end, comprising:
  a self-powered lighting unit that is readily detachable from the surgical tool and is readily attachable instead to an anatomical site within the confined space at the user's option.

In yet another aspect of the invention, there is provided a method of providing lighting at an operation site within a confined space to enable a user to operate therein any surgical tool that is not specifically configured for mounting of a lighting unit, comprising the steps of:

provide a compact, self-powered lighting unit actuated to deliver light from one end; and at the user's option, mounting the lighting unit to the tool or to a location entirely in the confined space so as to enable the delivered light to illuminate a selected region within the confined space.

These and other related aspects and benefits of the disclosed invention and its obvious variations will be better understood from the detailed description provided below with appropriate reference to the appended drawing figures.

DETAILED DESCRIPTION OF THE PREFERRED EMBODIMENTS

Figure 1:
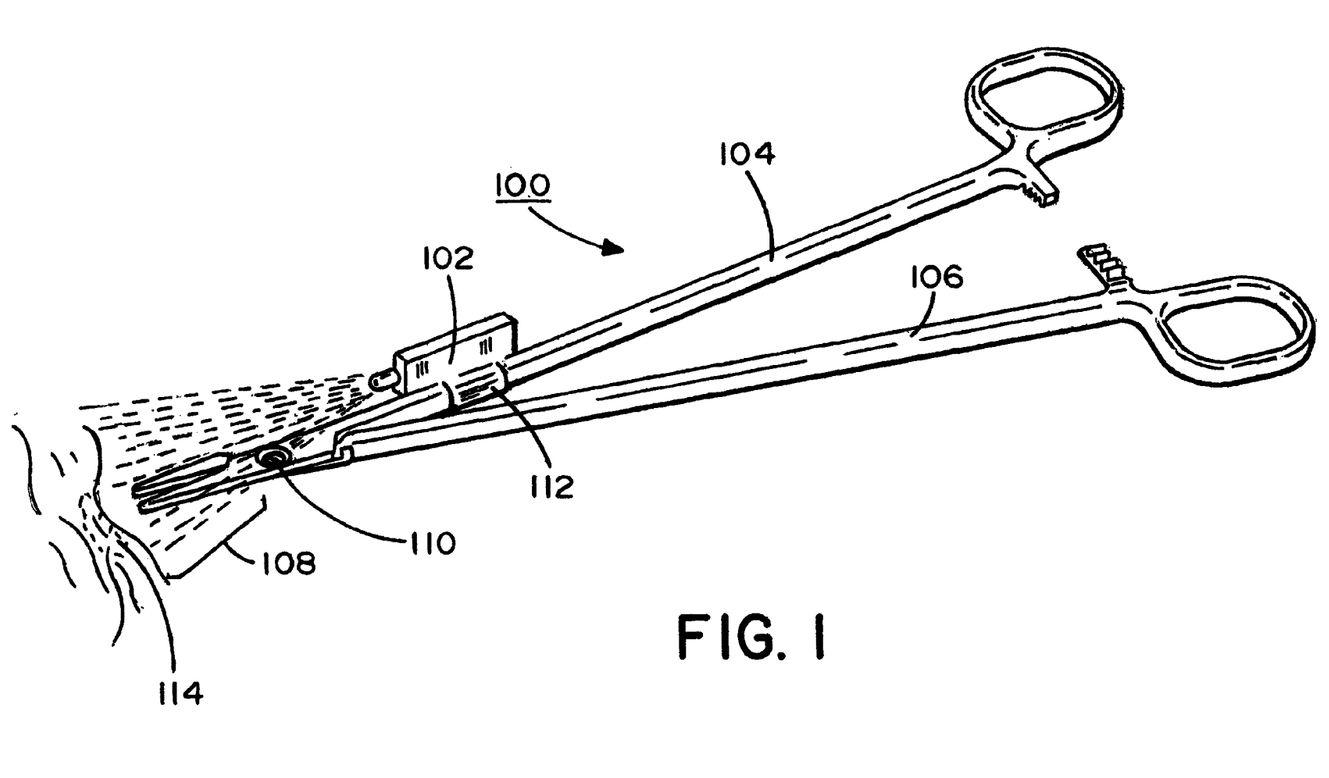
FIG. 1 presents a surgical instrument with attached surgical illumination device in accordance with an embodiment of the present invention.

FIG. 1 presents the principal elements of a compact, self-powered, selectively-mountable lighting unit which provides light directable by a user to an operation site in a confined space to enable the user to operate a tool therein. The lighting unit of the embodiment shown in FIG. 1 is detachably mountable to, for example, a surgical instrument so as to provide lighting of selected frequency range, in adjustable focus ranging from substantially diffuse to tightly focused beam, at and about an operating distal end of the instrument to facilitate accurate viewing thereat.

FIG. 1 presents a surgical instrument 100, such as an incision, cautery, clamping, irrigation, suturing, or tissue manipulation tool. The instrument 100 includes, for example, handles 104, 106, a pivot point 110, such as a screw or pin, and operative extension, such as shears 108. The instrument 100 is used, for example, to perform various surgical activities on human tissue 114. In accordance with an embodiment of the present invention, a surgical illumination device 102 shown is attached via an attachment feature 112 to the instrument 100 and is optionally directable so as to illuminate the tissue 114 during such activities.

In various embodiments of the present invention, as described further below, the illumination device 102 includes directable or general illumination features, such as one or more LEDs. The attachment feature 112, includes, for example, flexible attachment strips having such easily attachable features as Velcro™; adjustably coupleable straps, such as tie-wraps, also commonly known as cable ties; flexible flange and lip extensions; surgically compatible adhesive strips or glues; or other attachable and optionally detachable components, such as suction cups. The attachment feature 112 is attached to the illumination device at, for example, the base of the illumination device 102. Thus the illumination device 102 is an attachment that can be readily mounted at any selected location on any surgical tool without modification or special configuration of the surgical tool itself to enable it to receive a lighting unit. Furthermore, the illumination device 102, depending on the attachment feature 112, is optionally attachable to a surgical instrument or, at the user's option, to other surgically related locations such as adjacent human tissue.

Figure 2:
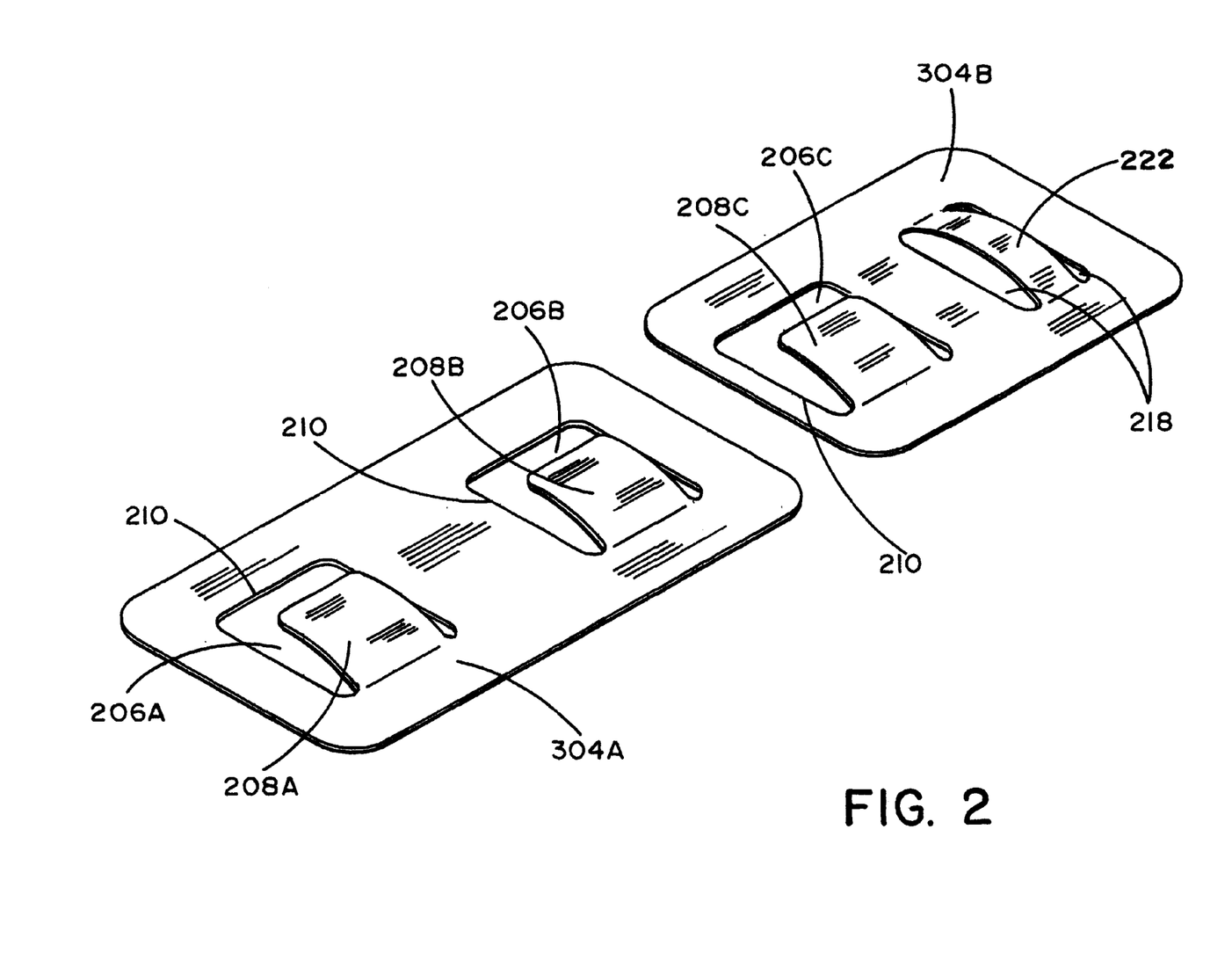
FIG. 2 shows a two piece electrically conductive component for use with an embodiment of the present invention.
Figure 3A:
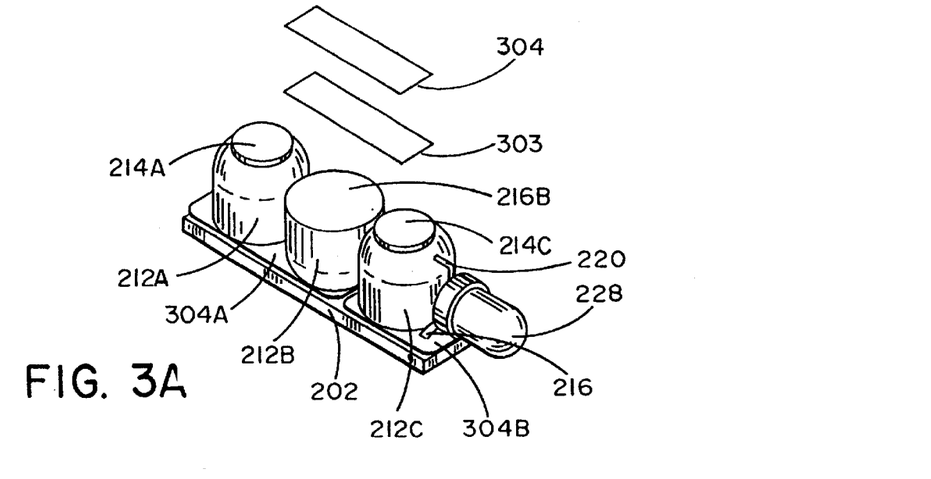
FIGS. 3A–3F show the components of a surgical illumination device in various states of assembly, in accordance with an embodiment of the present invention.
Figure 3B:
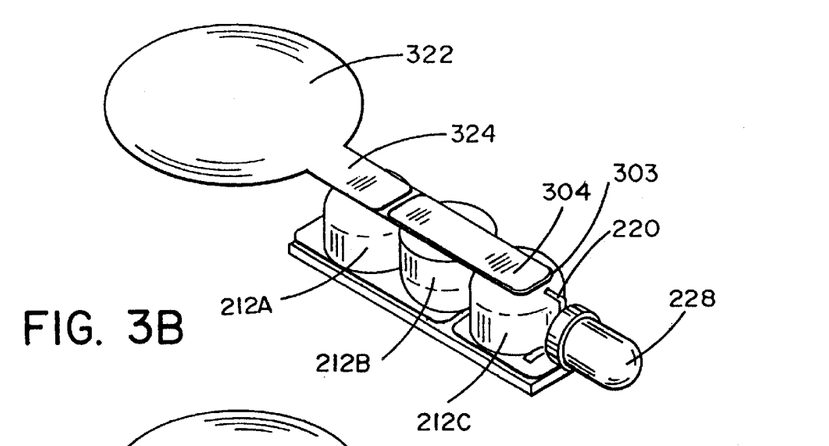
Figure 3C:
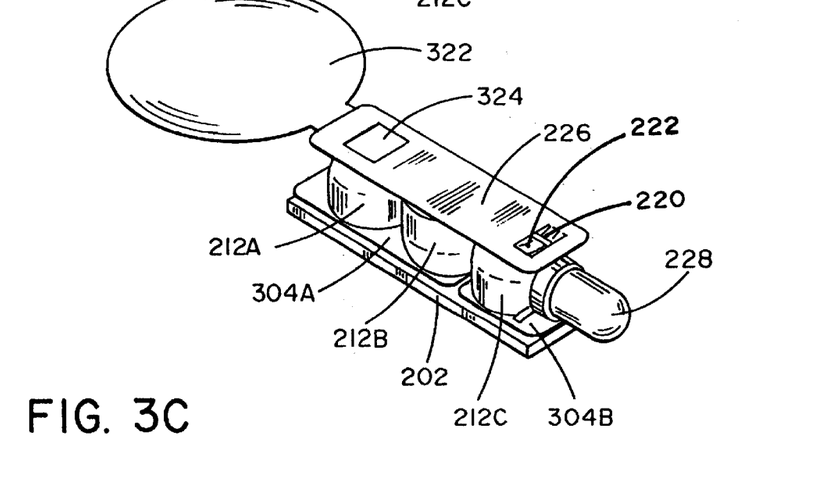

As best seen in FIGS. 3A–3C, various components are initially stacked on a base 202. Thus, directly on base 202 is placed a first pair of electrical conductors 304A, 304B, which, as best seen in FIG. 2, have lanced-in generally "C"-section cuts 206A, 206B, 206C that provide respective cantilevered and deliberately arced extensions 208A, 208B, 208C that rise above the surrounding periphery 210. Cuts 206A, 206B, 206C and their respective internal extensions 208A, 208B, 208C are spaced apart in accordance with power cells or batteries 212A, 212B, 212C. Each battery 212A, 216B, 212C has a central positive terminal 214A, 214B, 214C, and an outer negative terminal 216A, 216B, 216C, respectively, and is typically capable of providing a predetermined amount of power (from a fresh or fully-charged state) at a relatively steady voltage. To obtain adequate lighting for a suitable period of time to give the surgeon uninterrupted steady and consistently intense illumination of the operation site, it is preferable to utilize a plurality of small batteries 212 connected in series (as best understood with reference to FIG. 4). Reference back to FIG. 3A shows why the batteries are placed over conductive elements 304A, 304B so that their positive and negative poles are connected as desired and as clearly shown in the circuit diagram per FIG. 4. Preferred batteries are Eveready Type 393.

The combined voltage of the plurality of batteries 212A, 212B, 212C is delivered to a lighting unit 228 via an arced contact 216, as best seen in FIG. 3A. Negative outer terminal 214A of first battery 212A contacts conductive element 304A at arced extension 208A. A second contact 214B on a second battery 212B also contacts conductive element 304A at arced extension 208B. Negative terminal 216C on a third battery 212C contacts conductive element 304B at arced extension 208C. Conductive element 304B makes contact with light-generating element 228 containing the LED via contact 222, as best seen in FIG. 3C. Contact 222 is curved upward to provide, just liked curved arced extensions 208A, 208B and 208C , a springiness to ensure firm electrical contact with cooperating elements contacted thereby. Conducting element 303 enables negative terminal 216B to electrically connect with positive terminal 214C, as best seen in FIG. 3A. Finally, electrically conductive element 226, best seen in FIG. 3C, enables completion of the electrical circuit by enabling electrical connection between positive terminal 214A and contact 220 of the LED 228 only when non-conductive strip 324 is removed as described more fully below.

The desired light is preferably generated by a light-emitting diode (LED) 228, which receives the combined battery voltage via contact 216 and a corresponding contact 220 (best seen in FIG. 3A). An LED is preferable to a conventional incandescent lamp for its small size, higher efficiency, and lower operating temperature and heat release. It is noteworthy that the problem of collateral heat release from an operating LED has been addressed in U.S. Pat. No. 6,028,694 to Schmidt titled "Illumination Device Using Pulse Width Modulation of a LED." The teaching of this patent, to the extent that it teaches reduction of LED heat-output during operation, is incorporated herein by reference. A suitable LED for use in the present invention is BP280CW4K-3.6Vf-050T, manufactured by LEDtronics, of Torrance, Calif., USA. With three of the preferred batteries and such an LED, it is considered that the lighting unit should provide uninterrupted constant light for not less than 40 minutes. Under most operating conditions, this could easily be up to 50 minutes, and this should be adequate for most surgical procedures requiring such lighting.

However, if the operation at hand is complex, and must be conducted over a longer period of time, it becomes important that the user be warned shortly before battery power becomes exhausted. The user can then avoid starting a difficult or sensitive procedure until a fresh lighting unit has been fitted to the medical instrument in user or a replacement instrument is provided that has a fully-powered lighting unit mounted thereto. Surgery is often very demanding, and a surgeon who has held a particular instrument for a time may simply prefer to have a new lighting unit installed on the particular instrument he is holding in a quick replacement step, instead of releasing the instrument to grasp a new one. As discussed more fully below, detachment of one lighting unit from an instrument or other location, and replacement by another lighting unit, can all be accomplished in literally a matter of a few seconds in a variety of ways.

Figure 4:
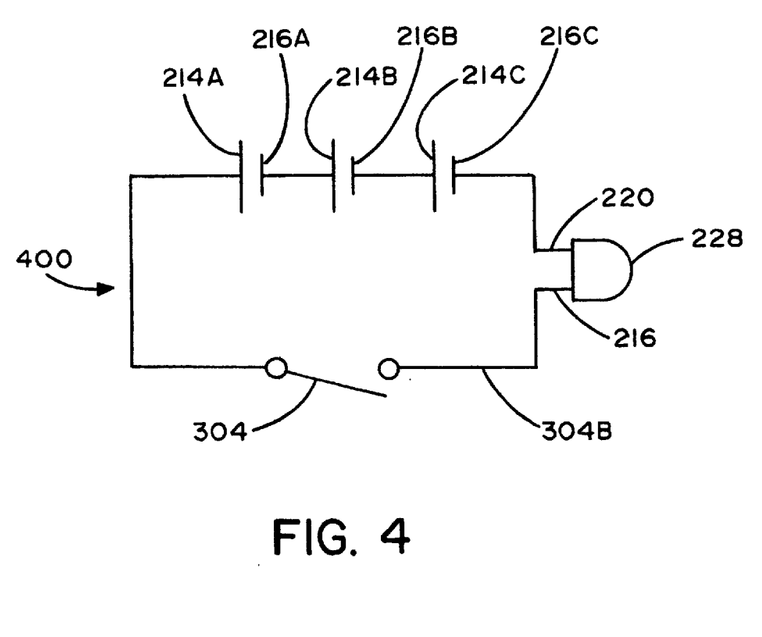
FIG. 4 is a circuit diagram of a circuit for a surgical illumination device in accordance with an embodiment of the present invention.

Various circuit elements exist that are small enough and demand very little power and are therefore suitable for inclusion in the circuit 400 per FIG. 4 to generate the desired warning of impending power exhaustion. Such an element could be a solid-state microcircuit, like that of an alarm on a digital battery-powered wrist-watch arranged so as to start timing when lighting unit 102 is activated, and to sound an audible alarm when a predetermined period of use has expired. Another option is to include in circuit 400 a subsidiary capacitance circuit that will react when the total delivered voltage from batteries 212A–212C diminishes past a preset reference voltage. Such a device could then actuate an audible signal generator or cause a brief flashing of the delivered light as a visible warning signal. Optionally, it could be used to provide both audio and visual warnings. Since available options are many and are well-known and commercially available it is not considered necessary to provide operational details of such circuit elements here.

Referring back to FIGS. 3B and 3C, it is seen that a generally "lollipop" shaped electrically non-conductive element 322 is placed on top of the upper positive terminal 214A of battery 212A. The key is that the strip-like portion 324 of non-conducting element 322 be sized and placed initially to prevent electrical contact between battery 212A and a second conductive element 226 placed thereon, as best seen in FIG. 3C. Conductive element 226 is formed along the same principles as elements 304A, 304B described earlier (i.e., with lanced-in and springy contacts spaced to contact the battery 212A and to deliver power therefrom via contact 220, as best understood with reference to FIG. 3C, to the light-generating element 228 containing the LED). As will be readily understood, forcible removal of non-conducive element portion 324 from between the upper terminal 214A of the battery 212A and conductive element 326 activates the circuit and delivers power to generate light.

Conductive element 304A places batteries 212A, 212B in series, and conducting element 304B connects the terminal 216C of battery 212C to light-generating element 228 containing the LED. Conductive element 303 and nonconductive element 304 are sandwiched between conductive element 226 and terminals 216B, 214C of batteries 212B, 212C, respectively. Non-conductive element 304 prevents shorting between conductive element 326 and conductive element 303. Conductive element 303 connects terminals 216B, 214C of batteries 212B, 212C, respectively, so as to place batteries 212B, 212C in series.

Figure 3D:
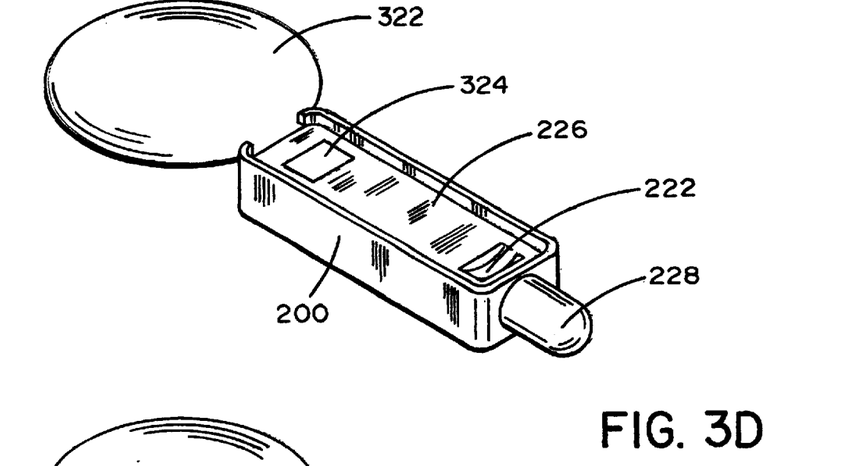
Figure 3E:
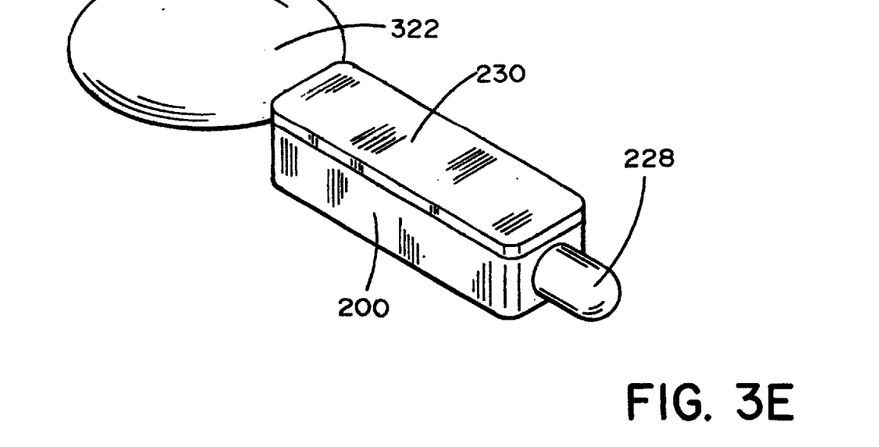
Figure 3F:
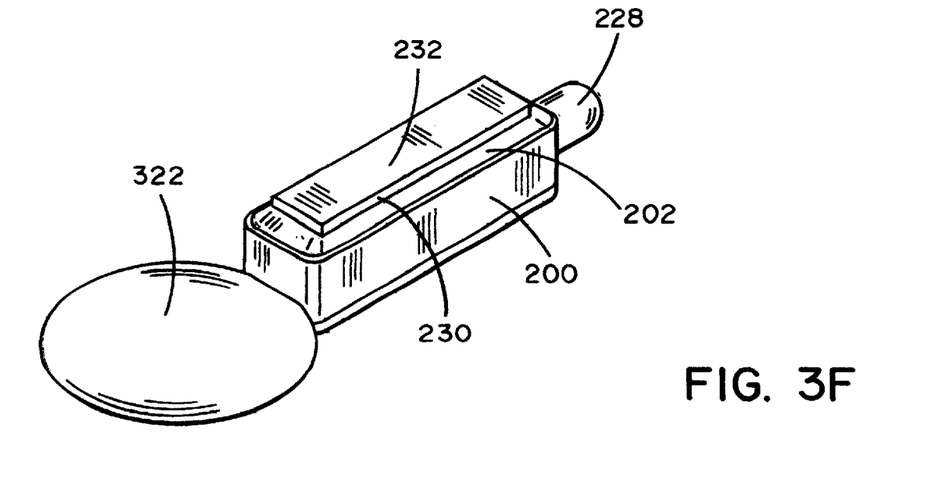

As best understood with reference to FIGS. 3D–3F, a peripheral wall is placed to surround the above-described components, with its bottom edge fitted tightly to and around a base 202 to which it may be adhered or heat-fused to be made integral therewith. Non-conductive element 322 (especially the strip-like portion 324) needs to be only paper-thin, and is preferably made of a strong plastics material such as Mylar™. What is shown as a circular outer end of the non-conductive material serves only as a user-graspable tab, and may be made of any convenient shape or thickness.

Finally, per FIG. 3E, a top or cover portion 230 is placed over and adhered or heat-fused to the upper periphery of the casing wall 2D to complete the structure of the lighting unit. As is readily seen from FIG. 3D, the LED-containing, light-generating element 228 extends out and forwardly of casing 200 via an appropriate aperture provided therein. A very shallow recess may be provided at the rear wall of casing 200 to initially accommodate the width and thickness of non-conductive portion 324 of the pull-out, one-time switch-ON element 322. Once element 322 is forcibly pulled out by the user the unit will be switched on and will continue to delivery light until the power supply is exhausted.

According to the first preferred embodiment, to base 202 there is adhered a compliant adhesive element 230 having an adherent surface initially covered with a removable protective cover sheet 232. See FIG. 3F. To mount this embodiment to a selected instrument or other support location, e.g., patient tissue close to the operation site if preferred by the surgeon, the protective cover sheet 232 must be removed and the now exposed adherent surface of adhesive element 230 firmly pressed to a mounting surface. The adhesive material employed here must be chosen with care to assure secure adhesion, complete separation for forced removal from the support, compatibility with patient tissue, initial sterilizability, and non-reactivity to any antibacterial or other substances likely to be contacted under normal conditions of use. Numerous such materials are now commercially available and persons skilled in the art are expected to make suitable choices therefrom. If the lighting unit is to be adhered to living, wet, or soft tissue in the patient's body the adherent material must also be non-allergenic and care must be taken when removing the lighting unit to avoid tissue damage.

Figure 5:
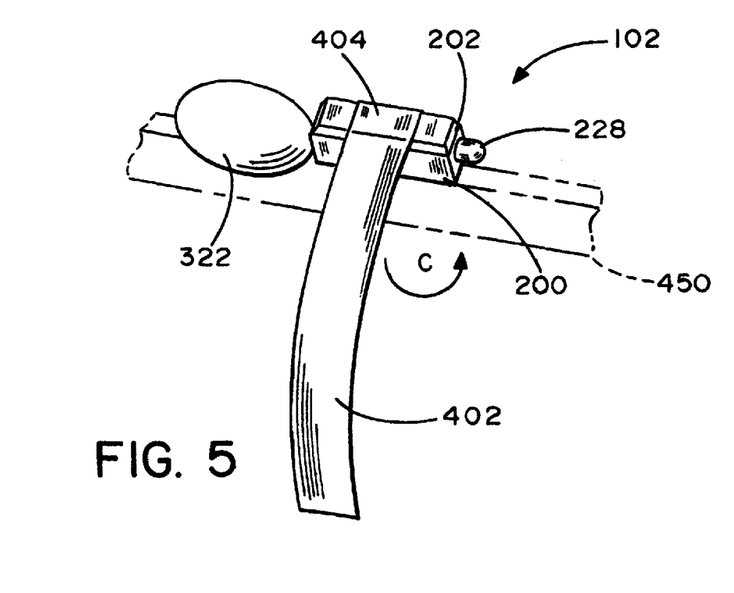
FIG. 5 presents a surgical illumination device with flexible strip fastener arrangement for attachment to, for example, a surgical instrument, in accordance with an embodiment of the present invention.

As best seen in FIG. 5, a second embodiment 400 comprises a flexible strip, e.g., the "loop" portion of a loop-and-hook VELCRO™ fastener arrangement instead of the direct adhesion technique per the first embodiment. In the second embodiment "loop" strip 402 is adhered or otherwise attached to base 202. Its length can then be used to circumscribe an elongate portion 450 of a surgical tool, as indicated by curved arrow "C", and then pressed to a firmly engageable "hook" portion 404 to mount the lighting unit to the medical instrument. In particular cases, it may be desirable to also have the adhesive element 232 per the first embodiment at the base of the lighting unit and to complement it with the flexible strip with the "loop-and-hook" arrangement 402, 404 per the second embodiment for more secure mounting.

Figures 6, 7, 8:
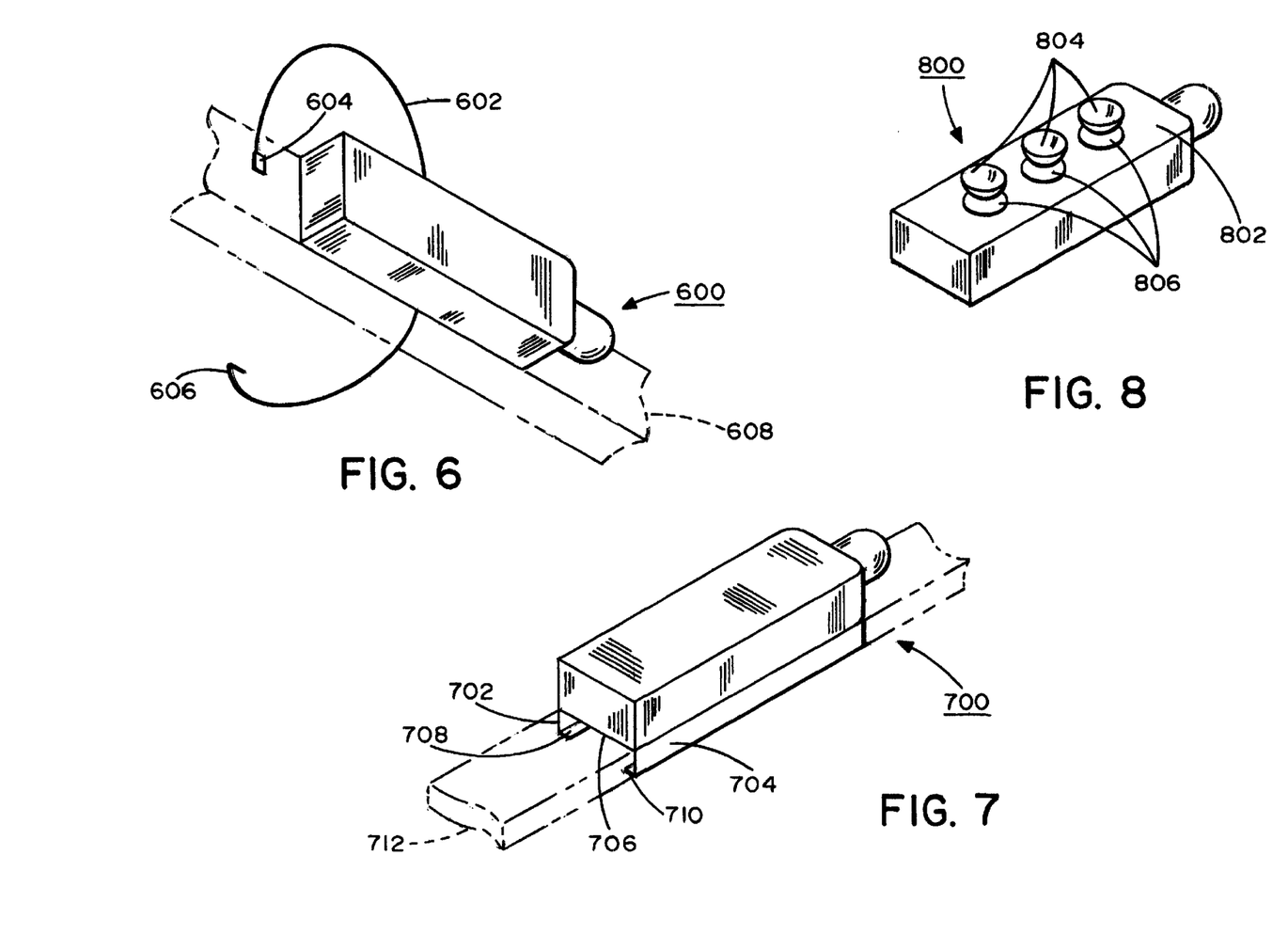
FIG. 6 shows a surgical illumination device having a flexible strip fastener with an adjustable attachment feature for attachment to, for example, a surgical instrument, in accordance with another embodiment of the present invention.
FIG. 7 is a surgical illumination device having flange and lip attachment features for attaching the device to, for example, a surgical instrument, in accordance with yet another embodiment of the present invention.
FIG. 8 is a surgical illumination device having small flexible suction cups on the base for attaching the device to, for example, a surgical instrument or human tissue, in accordance with a further embodiment of the present invention.

FIG. 6 shows a third preferred embodiment 600, in which is provided a flexible strip attached to the lighting unit body for mounting to an instrument. In this embodiment, one end of the flexible strip 602 has a first distal end with a loop-shaped opening 604 shaped and sized to receive and securely hold the other distal end 606 passed around the instrument body 608. The basic principle here is the same as in conventional cable ties (i.e., once end 606 is passed through loop 604 and pulled, it can only be tightened, but not slip back out). Excess length of the strip 602 at the distal end can then be cut off. Detachment of the lighting unit from instrument portion 608 is obtained by cutting strip 602 after use.

FIG. 7 shows yet another attachment option according to a fourth preferred embodiment, in which the casing light-unit 700 is formed to include two flanges 702, 704 at the opposite sides of the base 706, each flange having an inward lip (i.e., 708, 710, respectively). The flange and lip material must be firmly elastic and springy to grasp the instrument mounting portion 712. Flanges 702, 704 must also be sized to fit tightly to that particular mounting portion 712 as a tight clip. Such a clip-on arrangement can have any other known form to suit, for example instrument portions having round, elliptic octagonal or other cross-sections. Such variations on the basic theme are considered obvious modifications.

FIG. 8 shows a fifth preferred embodiment 800, in which base 802 is fitted with a plurality of small flexible suction cups 804 mounted on respective bases 806 that may be firmly adhered or otherwise attached to base 802. As will be readily visualized, all that a user has to do to mount this embodiment to an instrument mounting portion is to firmly press the suction cups 804 to a smooth, non-porous surface thereof. This embodiment may be particularly useful or mounting the lighting unit 800 to the patient's tissue, which, being wet, should provide good connection to the soft-flexible suction cups and also enable easy release without tissue damage.

As is made apparent in the foregoing description, the present invention provides a very compact, versatile, inexpensive, and safe lighting facility in very confined spaces to provide light of selected intensity and focus, exactly where needed by a user. If the task outlasts the power contained in one lighting unit, it can be replaced in mere seconds by another similar unit. The invention permits mounting to a user-operated instrument as well as to a support element close to the operation site to be lighted.

Further obvious modifications may add to the versatility and usefulness of the invention to sit particular needs. For example, a surgeon working on a very obese patient, in whom vaginal access during gynecologic surgery is particularly confined, may want a variation of the device with a "dead soft" extension provided between the lighting unit body and the light-generating LED. Such an arrangement could be mounted to tissue inside the patient, with the surgeon having more freedom to move the surgical instrument with a lighting device mounted near his line of sight. The surgeon could, as needed, adjust the "dead soft" support using his instrument to thereby adjust the direction and/or focus of the lighting.

It must be noted that although the best mode of the present invention was conceived as a solution to meet a particularly difficult problem in surgery its utility is considerably more extensive. A few examples will clarify what is meant by this.

For example, a telephone repairman working in darkness and possibly under adverse weather conditions to check out wiring in a confined wiring box may need to hold an elongate contact/probe in one hand and a dialed meter in another. The solution of holding a small flashlight in his mouth may not work too well for lighting an operation site amidst a maze of wiring. The small lighting unit according to the first or fourth embodiments, mounted to the elongate probe and adjustable for diffuse lighting for an overview and then to narrow focus for specific investigation and probing, would be far more efficient and comfortable. Essentially the same considerations apply to a technician trying to identify leaks of dangerous chemicals in the midst of complex and poorly lit piping, an automobile mechanic trying to operate on a bolt deep in a confined space in an automobile, or an antiquities restorer working to clean frescoes filled with crevices around the cupola of the a dark cathedral. This lighting device fitted directly to a tool held by the user to direct light precisely as and were needed can solve a variety of problems.

Finally, it is noted that in surgery it is very important for the surgeon to quickly see colors accurately. To an experienced surgeon, the hue and intensity of even a single basic color can convey significant information about the condition of particular tissues and hence the patient. White light is generally considered best for surgical applications but other colors, perhaps even ultra-violet light, may reveal details that might otherwise be easily missed during difficult viewing in a confined space. By careful choice of the LED (or an alternative known substitute therefor) a user can readily adapt the present invention to suit his needs.

Although the circuit per FIG. 4 is extremely simple, it lends itself to some obvious modifications to meet particular needs. For example, when the nonconductive element 222 is forcibly removed to permanently switch on the lighting unit 200 a very small opening will remain in the rear of the casing where the elongate strip 224 was removed. This, even if the entire unit was carefully sterilized before use, there is opened up the possibility of body or irrigation fluids loaded with electrolytes entering the inside of the lighting unit and reading the active circuit. Instead, a totally sealed and impenetrable unit can be made with a two-position, i.e., "ON" and "OFF", switch provided with a membrane cover. Such a variation would ensure against leakage problems and, also, allow the user to switch on the lighting at will and to switch it off to pause awhile or upon completion of a task.

Although the present invention has been described and illustrated in detail, it should be understood that the same is by way of illustration and example only and is not to be taken by way of limitation, the spirit and scope of the present invention being limited only by the terms of the appended claims.

What is claimed is:

1. A compact, self-powered lighting unit that is readily and detachably mountable to a user-selected location on any surgical tool that is not specifically configured for attachment of a detachable lighting unit, to provide lighting within a confined space containing a surgical site to enable a user to operate the surgical tool thereat, comprising:

a housing containing a power source;

a switchable circuit;

a light-generating element powered by the power source via the circuit; and a mounting mechanism attached to the housing, to enable the lighting unit to be selectively mounted to the surgical tool to provide lighting at and about the surgical site.

2. The lighting unit according to claim 1, wherein:

the light-generating element is adjustable to deliver light of variable focus ranging from substantially diffuse light to a narrow beam.

3. The lighting unit according to claim 1, wherein:

the circuit comprises a one-time on-switch which cannot be switched off after being switched on, having a movable non-conducting element initially positioned to prevent power flow to the circuit.

4. The lighting unit according to claim 1, wherein:

the circuit comprises an element for sensing when the power source is close to exhaustion and for then generating at least one of a visible or an audible signal to warn the user.

5. The lighting unit according to claim 1, wherein:

the lighting unit is totally sealed and the circuit comprises a membrane-covered switch actuable by the user to power the light-generating element at will.

6. The lighting unit according to claim 1, wherein:

the mounting mechanism comprises a mounting element selected from a group consisting of an adhesive element, a fastenable strip of flexible material, a suction cup, and a mechanical clip.

7. The lighting unit according to claim 1, wherein:

the power source comprises at least one cell.

8. The lighting unit according to claim 1, wherein:

the lighting comprises white light.

9. The lighting unit according to claim 1, wherein:

the power source is selected to provide continuous lighting of constant intensity for at least 40 minutes.

10. The lighting unit according to claim 1, wherein:

the housing is mountable at the user's option to a surface defining the confined space so as to provide light at and about the surgical site.

11. The lighting unit according to claim 1, further comprising:

a known dead-soft element cooperating with the light-generating element to enable the user to adjust orientation of the delivered light.

12. The lighting unit according to claim 1, wherein;

the housing is mountable to a user-selected portion of the surgical tool.

13. The improved tool according to claim 12, wherein:

the tool is a surgical tool selected from a group consisting of incision, cautery, clamping, irrigation, suturing, and tissue manipulation tools.

14. A compact, self-powered lighting unit mountable to any surgical tool selected by a user or at the user's option to tissue adjacent to an operation site in a confined space, to light an operation site in the confined space during use of the selected surgical tool by the user, comprising:

a housing containing a power source;

a switchable circuit;

a light-generating element powered by the power source via the circuit; and a mounting mechanism attached to the housing to enable the lighting unit to be selectively mounted as chosen by the user either to the surgical tool or to adjacent tissue to provide lighting at and about the operation site, wherein the light-generating element is adjustable to deliver light of variable focus ranging from substantially diffuse light to a narrow beam, wherein the circuit comprises an element for sensing when the power source is close to exhaustion and for then generating at least one of a visible or an audible signal to warn the user, wherein the lighting comprises white light, wherein the power source is selected to provide continuous lighting of constant intensity for at least 40 minutes, wherein the circuit comprises one of either a one-time on-switch having a removable non-conducting element initially positioned to prevent power flow to the circuit, or a membrane-covered switch actuable by the user to selectively actuate the circuit to power the light-generating element, and wherein the lighting unit is maintained in a medically sterile condition until shortly before use.

15. The lighting unit according to claim 14, further comprising:

a known dead-soft element cooperating with the light-generating element to enable the user to adjust orientation of the delivered light.

16. An improved surgical tool having an operating distal end that is to be used within a confined space where a user will require lighting at and about the distal end, the improvement comprising:

a self-powered lighting unit, that is readily mountable to the surgical tool at a location on the tool as selected by the user and is readily removable from the tool or at the user's option is attachable instead to an adjacent site in the confined space.

17. The improved tool according to claim 16, wherein:

the light-generating element is adjustable to deliver light of variable focus ranging from substantially diffuse light to a narrow beam.

18. The improved tool according to claim 16, wherein:

the circuit comprises a one-time on-switch having a removable non-conducting element initially positioned to prevent power flow to the circuit.

19. The improved tool according to claim 16, wherein:

the circuit comprises an element for sensing when the power source is close to exhaustion and for then generating at least one of a visible or an audible signal to warn the user.

20. The improved tool according to claim 16, wherein:

the lighting unit is totally sealed and the circuit comprises a membrane-covered switch actuable by the user to power the light-generating element at will.

21. The improved tool according to claim 16, wherein the tool has an elongate portion ending at the distal end, and the lighting unit is detachably attached to the elongate portion.

22. The improved surgical tool according to claim 16, further comprising:

a known dead-soft element attached to the lighting unit to enable the user to adjust orientation of light delivered therefrom.

23. A method of providing lighting at an operation site within a confined space to enable a user to operate therein any surgical tool not specifically configured to receive a lighting unit, comprising the steps of:

providing a compact, self-powered lighting unit actuated to deliver light from one end; and at the user's option, detachably mounting the lighting unit either to a user-selected portion of the tool or to an adjacent location within the confined space so as to enable light delivered from the lighting unit to illuminate a selected region within the confined space.

24. The method according to claim 23, wherein:

the lighting unit is mounted to the tool by a mounting element selected from a group consisting of an adhesive element, a fastenable strip flexible material, a suction cup, and a mechanical clip.

25. The method according to claim 23, comprising the further step of:

providing the lighting unit with an element for sensing when power available to operate the same is about to be exhausted and for then generating a corresponding visual or audible warning signal for the user.

26. The method according to claim 23, comprising the further step of:

adjusting the delivered light to a desired focus within a range from substantially diffuse to narrow beam.

27. The method according to claim 23, comprising the further step of:

adjusting the orientation of the delivered light.

* * * * *